US005610042A

United States Patent [19]
Chang et al.

[11] Patent Number: 5,610,042
[45] Date of Patent: Mar. 11, 1997

[54] METHODS FOR STABLE TRANSFORMATION OF WHEAT

[75] Inventors: Yin-Fu Chang, Carrboro, N.C.; James R. Wong, Milpitas, Calif.; Andrea Itano, Berkley, Calif.; Stephen J. Mejza, Union City, Calif.; Leslie Walker, Littleton, Colo.

[73] Assignee: Ciba-Geigy Corporation, Tarrytown, N.Y.

[21] Appl. No.: 147,261

[22] Filed: Nov. 1, 1993

Related U.S. Application Data

[63] Continuation-in-part of Ser. No. 992,391, Dec. 16, 1992, abandoned, which is a continuation-in-part of PCT/US92/08466, Oct. 5, 1992, which is a continuation-in-part of Ser. No. 772,435, Oct. 7, 1991, abandoned.

[51] Int. Cl.$^6$ .............................. A01H 5/00; C12N 15/87; C12N 15/82; C12N 15/90
[52] U.S. Cl. ...................... 435/172.3; 435/430; 800/205; 800/DIG. 58; 935/52; 935/53; 935/85
[58] Field of Search .............................. 435/172.3, 240.5, 435/240.48; 800/205; 935/52, 53, 85

[56] References Cited

U.S. PATENT DOCUMENTS

| | | | |
|---|---|---|---|
| 4,801,545 | 1/1988 | Stuart et al. | 435/240.4 |
| 5,036,006 | 7/1991 | Sanford et al. | 435/170.1 |

FOREIGN PATENT DOCUMENTS

| | | |
|---|---|---|
| 0245898 | 11/1987 | European Pat. Off. |
| 0331083 | 2/1989 | European Pat. Off. |
| 0397413 | 11/1990 | European Pat. Off. |
| 0442174 | 8/1991 | European Pat. Off. |
| WO91/02071 | 2/1991 | WIPO |
| WO92/09696 | 6/1992 | WIPO |
| WO93/04178 | 3/1993 | WIPO |
| WO93/07256 | 4/1993 | WIPO |
| WO9318168 | 9/1993 | WIPO |

OTHER PUBLICATIONS

Klein et al 1988 Bio/Technology 6:559–563.
Cao et al 1990 In Plant Gene Transfer, UCLA Symposium Mol. Cell. Biol., New Ser., vol. 129 pp. 21–34.
Bower, R., et al., "Transgenic Sugarcane Plants vis Microprojectile Bombardment":, *The Plant Journal*, 2(3):409–416 (1992).
Chang, Y.-F, et al., "An Anther Culture–derived System for Transformation Studies in Wheat (*Triticum aestiuum* L.)", Abstract Y105, *J. Cell. Biochem. Suppl.*, (Symposium Apr., 1992, Crop Improvement Via Biotechnology), 16F:205 (1992).
Chibbar, R. N., et al., "Transient Expression of Marker Genes in Immature Zygotic Embryos of Spring Wheat (*Triticum aestivum*) Through Microprojectile Bombardment", *Genome*, 34(3):453–460 (1991).

Christou, P., et al., "Production of Transgenic Rice (*Oryza sativa* L.) Plants from Agronomically Important Indica and Japonica Varieties via Electric Discharge Particle Acceleration of Exogenous DNA Into Immature Zygotic Embryos", *Biotechnology*, 9(10):957–962 (1991).
Kartha, K. K., et al., "Gene Transfer in Cereals Using Microprojectile Bombardment Technology", Abstract A2–77, *Abstracts with International Congress on Plant Tissue and Cell Culture*, (held in Amsterdam, Jun. 24–29, 1990).
Kartha, K. K., et al., "Genetic Engineering of Wheat Through Microprojectile Bombardment Using Immature Zycotic Embroys", Abstract Y001, *J. Cell. Biochem. Suppl.*, (Symposium Apr., 1992, Crop Improvement Via Biotechnology), 16F:198 (1992).
Orshinsky, B. R., et al., "Improved Embryoid Induction and Green Shoot Regeneration from Wheat Anthers Cultered in Medium with Maltose", Abstract 34766, *Biological Abstracts*, 91(4):AB–11 (1991).
Perl, A., et al., "Improvement of Plant Regeneration and GUS Expression in Scutellar Wheat Calli by Optimization of Culture Conditions and DNA–Microprojectile Delivery Procedures", *Mol. Gen. Genet.*, 235(2/3), 279–284 (1992).
Ozias–Akins et al., "Plant Regeneration from Cultured Immature Embryos and Inflorescences of *Triticum aestivum* L. (wheat) : Evidences for Somatic Embryogenesis", *Protoplasma*, 110:95–105 (1982).
Chang et al., "Plant Regeneration from Protoplasts Isolated from Long–term Cell Cultures of Wheat (*Triticum aestivum* L.)" *Plant Cell Reports*, 9:611–614 (1991).
Daniell et al., "Transient Expression of β–glucuronidase in Different Cellular Compartments Following Biolistic Delivery of Foreign DNA into Wheat Leaves and Calli", *Plant Cell Reports*, 9:615–619 (1991).
Dekeyser et al., "Evaluation of Selectable Markers for Plant Transformation", *Plant Physiol.*, 90:217–213 (1989).
Eicholtz et al., "Expression of Mouse Dihydrofolate Reductase Gene Confers Methotrexate Resistance in Transgenic Petunia Plants", *Somatic Cell and Molecular Genetics*, 13(1):67–76 (1987).
Hauptmann et al., "Evaluation of Selectable Markers for Obtaining Stable Transformants in the Gramineae", *Plant Physiol.*, 86:602–606 (1988).
Klein et al., "Transfer of Foreign Genes into Intact Maize Cells with High–Velocity Microprojectiles", *Proc. Natl. Acad. Sci.*, USA, 85:4305–4309 (1988).
Meijer et al., "Transgenic Rice Cell Lines and Plants: Expression of Transferred Chimeric Genes", *Plant Molecular Biology*, 16:807–820 (1991).

(List continued on next page.)

*Primary Examiner*—Patricia R. Moody
*Attorney, Agent, or Firm*—James Scott Elmer; Gary M. Pace

[57] ABSTRACT

The present invention is drawn to the production of fertile transformed wheat plants. The method involved subjecting wheat tissues to high velocity microprojectile bombardment, selecting for transformed cells, and regenerating stably transformed fertile plants from the transformed cells.

5 Claims, 2 Drawing Sheets

OTHER PUBLICATIONS

Oard, et al., "Transient Gene Expression in Maize Rice, and Wheat Cells Using an Airgun Apparatus", *Plant Physiol.*, 92:334–339 (1990).

Redway et al., "Identification of Callus Types for Long–term Maintenance and Regeneration from Commercial Cultivars of Wheat (*Triticum aestivum* L.)" *Theor. Appl. Genet.*, 79:609–617 (1990).

Redway et al., "Characterization and Regeneration of Wheat (*Triticum aestivum* L.) Embryogenic Cell Suspension Cultures", *Plant Cell Reports*, 8:714–717 (1990).

Sanford, J. C., "Biolistic Plant Transformation", *Physiologica Plantarum*, 79:206–209 (1990).

Vasil et al., "Herbicide Resistant Fertile Transgenic Wheat Plants Obtained by Microprojectile Bombardment of Regenerable Embryogenic Callus", *Bio/Technology*, 10:667–674 (1992).

Vasil et al., "Rapid Production of Transgenic Wheat Plants by Direct Bombardment of Cultures Immature Embyros", *Bio/Technology*, 11:1553–1558 (1993).

Wang et al., "Transient Expression of Foreign Genes in Rice, Wheat and Soybean Cells Following Particle Bombardment", *Plant Molecular Biology*, 11:433–439 (1988).

Wang et al., "A Novel Approach for Efficient Plant Regeneration from Long–term Suspension Culture of Wheat", *Plant Cell Reports*, 8:639–642 (1990).

Weeks et al., "Rapid Production of Multiple Independent Lines of Fertile Transgenic Wheat (*Triticum aestivum*)", *Plant Physiol.*, 102:1077–1084 (1993).

METHODS FOR STABLE TRANSFORMATION OF WHEAT

The present application is a continuation-in-part of: U.S. application Ser. No. 7/992,391, (filed Dec. 16, 1992, now abandoned), which is a continuation-in-part of PCT application International No. PCT/US92/08466, filed Oct. 5, 1992, which is a continuation-in-part application of U.S. application Ser. No. 07/772,435, filed Oct. 7, 1991, (now abandoned), which disclosures are herein incorporated.

FIELD OF THE INVENTION

The present invention relates to the transformation and regeneration of fertile transformed plants, particularly wheat.

BACKGROUND OF THE INVENTION

Wheat is one of the most important cereal crops in the world. While it is currently being grown in a wide range of environments, the most prominent production of wheat occurs in the U.S.A., China, Australia, Canada, India and Europe.

Most of the wheat production is consumed as flour. Bread wheat accounts for about 80% of total consumption of wheat.

The development of an efficient transformation system is necessary for the molecular analysis of gene expression in plants. In cereal crop plants, this development has been slowed by difficulties encountered in plant regeneration and in the insusceptibility of monocots to *Agrobacterium* mediated transformation. Most of the progress that has been made in the transformation of cereals has been in producing transgenic flee and maize. The progress in wheat has been hampered by the inability to establish suitable techniques for the regeneration of fertile plants following transformation.

There are a number of published reports of transient expression of foreign genes in wheat. However, the only report of stably transformed wheat plants involves a labor intensive method which yields transformants at a low frequency.

Thus, there is a need for biotechnological methods for the development of high-yield, high-nutritional, and disease-resistant wheat varieties. Such methods are necessary to complement the traditional breeding methods currently in use.

SUMMARY OF THE INVENTION

The present invention is drawn to methods and compositions for the stable transformation of wheat with nucleic acid sequences of interest and the regeneration of fertile transgenic wheat plants. Particularly, wheat tissues are transformed using high velocity microprojectile bombardment and stably transformed plants regenerated. The method produces stably transformed fertile wheat plants capable of producing progeny which are stably transformed and which express the foreign gene of interest.

DETAILED DESCRIPTION OF THE INVENTION

A rapid, highly efficient method for the stable transformation of wheat cells and the regeneration of transgenic wheat plants is provided. The method involves stably transforming a wheat cell and regenerating wheat plants from transformed wheat cells. In addition, using the methods of the invention, fertile transgenic wheat plants can be grown to maturity with a high frequency. The fertile transformed plants are capable of producing transformed progeny that express the foreign gene(s).

The method involves subjecting wheat tissues to high velocity microprojectile bombardment using nucleic acid or particularly, genes of interest. Wheat tissues that are capable of transformation according to the methods of the invention include calli, cell suspension cultures, anthers, microspores, embryos, inflorescences, and the like. Cell suspension cultures can be derived from calli of embryos, leaf tissues, young inflorescences, anthers, etc.

Callus can be originated from any tissues of wheat plants including *Triticum aestivum* and *Triticum durum*. Preferably the tissue utilized in initiating callus is immature tissue such as immature embryos, immature inflorescences, and the basal portion of young leaves. Alternatively, callus can be originated from anthers, microspores, mature embryos and in principle any other tissue of wheat capable of forming callus and or secondary embryos. An especially useful tissue for producing regenerable callus is the scutellum of immature wheat embryos. Herein, the term callus refers to regenerable callus, further divisible into Type I callus and Type II callus as defined in corn (See, for example. Ozias-Atkins et al. (1982) Protoplasma 110:95–105; Maddock et al (1983) J. of Experimental Botany 34(144):915–926; Green (1982) In: Fujiwara A. (ed) Proc. 5th Intl. Cong. Plant Tissue and Cell Culture, Maruzen Co., Tokyo, pp. 107–108; Green et al. (1982) In: Downey K. et al. (eds) Molecular genetics of Plants and Animals, Miami Winter Symposium Series, Academic Press, New York, pp. 147–157; and Tomes (1985). In: Bright S. (ed) Cell Tissue and Cell Culture, Martinus Nijhoff/Dr. W. Junk Publishers, Dordrecht, The Netherlands, pp. 175–203).

Figure 1:
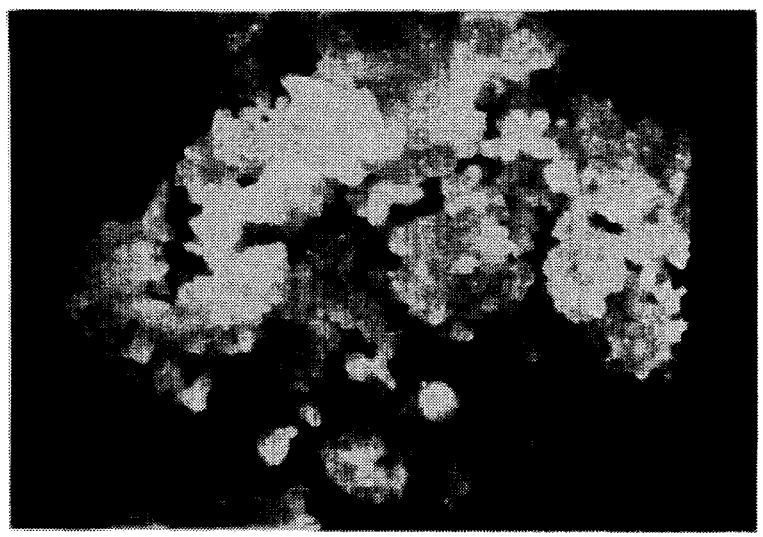
FIG. 1 shows wheat Type II callus induced from immature embryos.

Callus useful in the method of the invention includes Type I and Type II callus (FIG. 1) induced from explants cultured on a medium containing sucrose or other carbohydrate source. Of particular interest is callus which has been derived from immature embryos cultured on a medium containing maltose, hereafter referred to as Type M callus. In plant tissue culture, particularly in cereal immature embryo culture, sucrose has been used almost exclusively as the energy source, usually at levels of 2–3%. Maltose has been reported to have improved green plant regeneration from alfalfa petioles and wheat anthers. (See, for example, Strickland et al. (1987) Plant Science 48:113–121; Stuart et al. U.S. Pat. No. 4,801,545; Brettell et al. (1990) Plant Cell Reports 9:14–16; Orshinsky et al. (1990) Plant Cell Reports 9:365–369; and Zhou et al. (1991) Plant Cell Reports 10:63–66).

It is recognized throughout the steps of the invention that the method involves growth of callus or plant tissues on tissue culture medium. Generally useful throughout the method described herein is the use of a basal medium comprising micronutrients, macronutrients, a carbon source, iron, vitamins, and plant growth regulators. Plant growth regulators are known in the art and include auxins, cytokinins and gibberellins. Such regulators may depend on the step in the process and the particular wheat genotype utilized.

Figure 2:
FIG. 2 shows wheat Type M callus induced from immature embryos.

Type M callus (FIG. 2) can be obtained directly from culturing immature embryos on maltose-containing medium. The maltose-induced embryo callus is friable, granular with visible somatic embryos, and relatively slow growing. Maltose may be added into the tissue culture medium at a level of about 1 to about 30%, preferably about 11 to about 18%. The exposure time of embryos to maltose may range from about 3 to about 42 days, preferably about 7 to about 28 days.

Plant growth regulators useful in the invention include those with auxin-like functions such as IAA, NAA, 2,4-D, 2,4,5-T dicamba, p-chlorophenoxyacetic acid and the like. Such regulators may be added to the maltose-containing medium at a level of about 0.5 mg/l to about 100 mg/l, preferably about 1 mg/l to about 40 mg/l, and most preferably about 2 to about 10 mg/l, 2,4-D is the preferred plant growth regulator for inducing Type M callus from wheat immature embryos cultured on a maltose-containing medium.

The Type M callus may be used as a target tissue for transformation. It is also used directly in generating cell suspension cultures or in generating Type II callus. By utilizing Type M callus or Type M-derived Type II callus, a regenerable cell suspension culture is obtained within 3 months from embryo culture. This is much shorter than the conventional method (at least 6 to 8 months) where sucrose is used as the major carbohydrate source in the medium. The Type M-derived Type II callus and the Type II-derived cell suspension cultures are also highly regenerable. Up to 400 plants can be regenerated per gram (fresh weight) of such Type II callus.

The Type M callus and Type M-derived Type II callus of the invention yield fertile plants and progeny. In fact, up to about 89% of the plants regenerated from 9-month-old Type M and Type M-derived Type II callus produce seeds. In addition, the Type M and Type II callus, and their derived cell suspension cultures are suitable for transformation. They yield a large number of transformants and fertile plants and progeny.

There are several advantages to using Type II callus as the target tissue. First Type II callus is friable. That is, the callus is characterized as small cell aggregates. The Type II callus of the invention is also highly competent for the establishment of regenerable cell suspension cultures, yields a large number of transformants, is highly regenerable and yields fertile plants and progeny. In general Type II callus culture is more amenable in bombardment protocols and for selection of transformed tissue.

General references for initiating callus include Green E. C. (1982) In: Fujiwara A (ed) Proc. 5th Intl. Cong. Plant Tissue and Cell Culture, Maruzen Co., Tokyo, pp. 107–108; and Maddock SE (1987) Plant Cell Rep 6:23–26.); anthers (See, for example Harris et al. (1988) Plant Cell Rep &:337–340, Jahne et al. (1991) Theor. Appl. Genet. 82:74–80, and Sun et al. (1989) Plant Cell Rep 8:313–316.

The tissue to be transformed is bombarded with a high velocity microprojectile bombardment device. High velocity microprojectile bombardment offers a rapid method for transformation. See, generally, Finer et al. (1992) Plant Cell Reports 11:323–328; Christou P. (1990) Physiologia Plantarum 79:210–212; Wang et al. (1988) Plant Molecular Biology 11:433–439; Daniell et al. (1991) Plant Cell Reports 9:615–619; Klein et al. (1988) Proc. Natl. Acad. Sci. U.S.A. 85:4305–4309; Klein et al. (1987) Nature 327:70–73; Gordon-Kamm et al. (1990) The Plant Cell 2:603–618; Oard et al. (1990) Plant Physiol. 92:334–339; Sanford J. C. (1990) Plysiologia Plantarum 79:206–209; Fromm et al. (1990) Bio/Technology 8:833–839; Christou et al. (1988) Plant Physiol. 87:671–674; Sautter et al. (1991) Bio/Technology 9:1080–1085; Iida et al. (1990) Theor. Appl. Genet. 80:813–816; and Christou et al. (1991) Bio/Technology 9:957–962.

While several particle bombardment devices are disclosed in the literature, a preferred device is the particle gun disclosed in U.S. patent application Ser. No. 772,435, herein incorporated by reference. Such disclosed particle gun is capable of introducing particles carrying genetic material into a wide variety of cells. The gun comprises:

a flying block to accelerate and direct particles carrying genetic material;

an inert gas driven launch device capable of precise flying block velocity control;

a stop/stripping arrangement to stop the flying block and allow free flight of the particles coded with genetic material toward intact cells; and attendant locks and safety features.

The gun has a rapid firing cycle as well as a consistent force and accuracy of the shots fired. The gun provides a controlled, reproducible, adjustable and safe propulsion source. An additional benefit of the gun disclosed in U.S. application Ser. No. 772,435 is that the gun requires less DNA for bombardment than other devices known in the art.

Generally the tissue is shot at least one time. However, multiple shots of the tissue may be performed to enhance transformation frequency. About two shots per transformation has been demonstrated to yield best results.

The particles used as DNA carders in the bombardments were generally about 0.5 to about 2.0 micron in diameter, more specifically about 1.0 micron. The particles are coated with at least about 0.5 ug to about 2.0 ug DNA per shot. Particles useful in the invention are commercially available. For example, gold particles from BioRad Company can be utilized.

The particle gun of U.S. application Ser. No. 772,435 allows for the control of the pressure. A pressure in the range of about 500 psi to about 2500 psi, preferably about 1900 psi may be utilized.

The tissue may be subjected to plasmolysis before bombardment, after bombardment, or preferably both before and after bombardment. Plasmolysis treatment may be performed by diluting cells in a liquid medium with added osmoticum or by transferring cells to semisolid medium containing plasmolyzing agent. Generally the osmoticum can be any sugar such as sorbitol, mannitol, sucrose and the like. The growth medium may additionally comprise auxin.

After bombardment the cells are grown for several days in the dark on growth medium with auxin. Typically the cells are grown for about 5 days to about 10 weeks, more specifically about 1 week to about 7 weeks, before subjected to selection pressure.

A number of selective agents and resistance genes are known in the art. (See, for example, Hauptmann et al. (1988) Plant Physiol. 86: 602–606; Dekeyser et al. (1988) Plant Physiol. 90: 217–223; Eichholtz et al. (1987) Somatic Cell and Molecular Genetics 13: 67–76; Meijer et al. (1991) Plant Molecular Biology 16: 807–820; and Dekeyser et al. (1989) 90: 217–223.) Inhibitors such as amino-glycoside antibiotics which interfere with the translation machinery of prokaryotic and eukaryotic cells, may be utilized. Such inhibitors include kanamycin, G418, hygromycin, etc. Such inhibitors can be inactivated by phosphorylation reactions mediated by the products of either the Tn 5 neomycin phosphotransferase II (npt-II) gene or the hygromycin B resistance gene from *E. coli*. (See, for example, Herrera-Estrella et al. (1983) EMBO J 2: 987–995); Waldron et al. (1985) Plant Mol Biol 5: 103–108; and the references cited therein.)

Additionally, selective agents such as bleomycin, methotrexate, and phosphinothricin can be utilized. Favorable results have been achieved utilizing methotrexate. Methotrexate binds to the catalytic site of the dihydrofolate reductase enzyme, resulting in a deficiency of thymidylate and subsequent cell death. (Weikheiser, W. C. (1961) J Biol Chem 236: 888–893.) Reports in the literature indicate that chimeric constructs containing a bacterial or mouse dhfr gene can confer resistance to low levels of methotrexate in transformed tobacco, turnip, petunia and rice plants. (See, DeBlock et al. EMBO J 3:1681–1689; Brisson et al. Nature 310: 511–514; Eichholtz et al. (1987) Somatic Cell and Molecular Genetics 13: 67–76; and Dekeyser et al (1989) Plant Physiol. 90: 217–223.)

After growth on selection medium the transformed and selected tissue is allowed to grow. After several weeks, from about 4 to about 30 weeks, the tissue is transferred to medium for regeneration.

One of the major obstacles to the production of transformed wheat plants has been methods for regeneration of plants from transformed tissues. Generally for plant regeneration, transformed callus is grown on either a hormone-free medium containing sucrose, on a medium containing a cytokinin, or on a medium containing auxin and gibberellin. The callus cultures are transferred to the light. Plant development is continued on a hormone-free medium or medium with auxin. After development of roots and shoots, plantlets are transferred to soil and grown to maturity.

At several stages along the process, DNA is extracted from the tissue (callus and plant) and probed to confirm transformation. Methods are available in the art for the isolation of DNA from callus and tissues as well as for confirming the presence of DNA of interest. Such methods to confirm include PCR analysis as well as Southern hybridization. See, Southern, E. M. (1975) J Mol Biol 98:503 and Mullis, K. B. (1987) Meth in Enzymology 155:335.

As will be evident to one of skill in the art, now that a method has been provided for the stable transformation of wheat, any gene of interest can be used in the methods of the invention. For example, a wheat plant can be engineered to express disease and insect resistance genes, genes conferring nutritional value, genes to confer male and/or female sterility, antifungal, antibacterial or antiviral genes, and the like. Likewise, the method can be used to transfer any nucleic acid to control gene expression. For example, the DNA to be transferred could encode antisense RNA.

In one embodiment of the invention, Type II callus is used as the target tissue. The callus tissue is shot twice with DNA coated 1.0 micron gold particles. Bombardment parameters include 1.0 micron particles; 2 shots per target; 0.6 ug DNA per shot; 1900 psi; with plasmolysis treatment both pre- and post-bombardment. About 14 days post-bombardment, the bombarded tissue is subjected to selection on methotrexate in the range of about 0.1 to about 20 ug/ml methotrexate, more specifically about 0.5 to about 5 ug/ml methotrexate for about four months. To regenerate fertile wheat plants from the transformed cells, the tissue is transferred to MS medium containing about 0.1 mg/l to about 1.0 2,4-D in the dark. After the tissue has formed embryogenic structures, it is transferred to MS medium containing about 0.5 to about 1 mg/l NAA, and about 0.5 to about 10 mg/l GA and placed in the light for about two weeks. After shoot induction the tissues are transferred to MS medium without hormones or half-strength MS containing about 0.1 to about 1 mg/l NAA for root induction.

Utilizing the methods described herein, a high efficiency of transformed callus lines is obtained compared to other published reports. In fact up to 50% efficiency can be seen as confirmed by PCR and/or Southern analysis. Transformation experiments routinely yield stable transformants at a frequency as high as about 50% based on the number of transformants obtained per number of targets shot. Furthermore, by utilizing methotrexate selection, regenerated plants test positive for transformation.

In another embodiment, the method can be used to transform embryos, mature or immature. In this method, spikes from greenhouse grown wheat plants are collected about 10 to about 16, generally about 12 days after anthesis. Kernels are separated from the spikes and surface sterilized. Embryos are then excised and plated on growth medium. 0 to 10 days post excision, DNA is delivered to the embryo using a particle bombardment device. After DNA delivery the embryo or developing callus can be maintained without selection pressure and then the tissue can be regenerated in the presence or absence of selection. Alternatively, plants are regenerated from the bombarded tissue without selection and regenerated plants tested for the presence of the delivered DNA.

Improved embryogenic cultures of wheat can be obtained by using previously regenerated material as a source of starting material. Such improved cultures are referred to as "recycled lines" since they are "cycled" through the tissue culture process more than once. The starting material for these improved cultures may be either immature embryos obtained directly from regenerated plants, or the starting material may be seeds from regenerated plants grown as a source of immature embryos. The embryogenic cultures so derived have improved initiation frequency and fertility of regenerants compared to traditional, non-recycled lines. These improvements significantly increase the ease and efficiency with which transgenic wheat and its progeny may be obtained.

Having generally described the invention, the following examples are offered by way of illustration and not by way of limitation.

EXPERIMENTAL

I. Preparation of wheat callus, genotype UC703

Wheat plants of genotype UC703 were grown to flowering and self-pollinated. Spikes containing embryos 1 to 2.5 mm in length were removed from the plants and sterilized with 10% Clorox solution for 10 minutes. Embryos were removed from the immature seeds and placed with the embryo axis downwards on the medium of Murashige and Skoog containing 5 or 10 mg/l 2,4-D, 13.7% w/v maltose, 100 mg/l proline and 100 mg/l myo-inositol solidified with 0.7–0.8% w/v phytagar or 0.1–0.2% gelrite (initiation medium). After a three week culture in the dark at 27° C., a preferred callus was recognized by the presence of well formed globular, somatic embryos (Type M callus) developing on the scutellum of certain explants. These calli were removed and placed either on MS medium containing 1.0 to 5.0 2,4-D and 2–3% sucrose or on a medium containing a reduced level (5%) of maltose before being placed on the sucrose medium. The material was then subcultured every week to fresh MS medium containing 3% sucrose.

II. Genotypic response of wheat in Type M callus induction

Wheat plants of genotype UC703, MIT, Orofen, Yecoro rojo and Chris were grown to flowering and self-pollinated. Immature embryos were removed from spikes and cultured on a Murashige and Skoog medium containing:

1 mg/l 2,4-D plus 2% sucrose (1MS), 1 mg/l 2,4-D plus 2% maltose (1MS2M), 1 mg/l 2,4-D plus 9% maltose (1MS9M), 1 mg/l 2,4-D plus 13.7% maltose (1MS13.7M), or 10 mg/l 2,4-D plus 13.7% maltose (10MS13.7M)

to induce Type M callus formation. After three weeks culture in the dark at 27° C., the induction frequency (%) of Type M callus, Type I callus, as well as non-morphogenic structures from the immature embryos of the tested genotypes were scored.

| Genotype name | Medium | Type M callus (%) | Type I callus (%) | Others |
|---|---|---|---|---|
| UC703 | 1MS | 0 | 38 | 62 |
| UC703 | 1MS2M | 0 | 0 | 100 |
| UC703 | 1MS13.7M | 13 | 59 | 28 |
| UC703 | 10MS13.7M | 60 | 14 | 26 |
| MIT | 1MS | 0 | 10 | 90 |
| MIT | 1MS2M | 0 | 0 | 100 |
| MIT | 1MS9M | 6 | 28 | 66 |
| MIT | 10MS13.7M | 13 | 51 | 36 |
| Orofen | 1MS2M | 0 | 0 | 100 |
| Orofen | 1MS9M | 6 | 39 | 55 |
| Yecoro rojo | 1MS13.7M | 33 | 10 | 57 |
| Yecoro rojo | 10MS13.7M | 12 | 0 | 86 |

III. Type M callus induction frequency from wheat genotype UC703.

Wheat plants of genotype UC703 were grown to flowering and self-pollinated. Immature embryos were removed from the spikes and placed with the embryo axis downwards on the medium of Murashige and Skoog (MS) containing 5 or 10 mg/l 2,4-D and 13.7% w/v maltose solidified with 0.8% phytagar. After 3 weeks culture in the dark at 27° C., the Type M callus induction frequency from the cultured immature embryos was scored.

| Medium 1. MS + 5 mg/l 2,4-D + 13.7% maltose | | |
|---|---|---|
| | No. of embryos produced | No. of embryos cultured | Type M callus |
| Rep 1 | 200 | 116 | |
| Rep 2 | 464 | 250 | |
| Rep 3 | 100 | 35 | |
| Total | 764 | 401 | |

Type M callus induction frequency: 52%

| Medium 2. MS + 10 mg/l 2,4-D + 13.7% maltose | | |
|---|---|---|
| | No. of embryos produced | No. of embryos cultured | Type II callus |
| Rep 1 | 400 | 184 | |
| Rep 2 | 375 | 175 | |
| Rep 3 | 125 | 41 | |
| Total | 900 | 400 | |

Type II callus induction frequency: 44%

IV. Cell Preparation for Bombardment

The cells for bombardment were given a plasmolysis treatment before and after bombardment. Packed cell volume was measured and cells were diluted in 1 MS liquid medium with added osmoticum: 0.4M sorbitol for suspension cells and 0.6M sorbitol for callus cells. Cells were diluted such that the final packed cell volume per target was 1/20 ml for a fine suspension and 1/10 ml for callus. Diluted cells were placed in a 250 ml flask containing a stir bar and stirred for a minimum of 30 minutes, up to a few hours. To plate the cells, 2 ml was withdrawn from the flask and pipetted into the top of a vacuum flask onto which a Whatman 2.5 cm GFA filter was placed. The vacuum was applied until the cells were dried onto the filter. The filters were placed on 60×15 mm petri plates containing 5 ml of solid post-bombardment plasmolysis medium: 1 MS containing 0.2M sorbitol for suspension cells, or 0.4M sorbitol for callus cells. Two filters were plated on each dish.

V. Vectors used for bombardment

Two plasmids were co-delivered to cells:

pSOG30 is comprised of the 35S-promoter, fused to introl 6 from alcohol dehydrogenase isozyme 1, fused to the translational leader from the Maize Chlorotic Mottle Virus, fused to beta-glucuronidase (GUS) gene, fused to the nopaline synthase terminator, cloned into the vector pUC18; and, pSOG35 is comprised of the 35S-promoter, fused to intron 6 from alcohol dehydrogenase isozyme 1, fused to the translational leader from the Maize Chlorotic Mottle Virus, fused to the dihydrofolate reductase gene from E. coli, fused to the nopaline synthase terminator, all cloned into the vector pUC18.

VI. Particle Preparation

Gold particles (1.0 micron; from Bio-Rad) were washed by aliquoting into a microfuge tube, adding ~1 ml 100% ethanol, vortexing, spinning down, removing the supernatant, and repeating twice with sterile water. After the final wash, as much water was removed as possible and polylysine solution (0.02% polylysine +15 mM ammonium acetate) was added to completely immerse the particles. The particles were vortexed, spun, and the supernatant removed. The particles were allowed to dry overnight in a laminar flow hood or for 30 minutes under a gentle nitrogen stream.

For a "full" particle preparation, 10 mg particles were weighed out and placed in a sterile microfuge tube containing a stir bar. 100 ul (1 ug/ul) DNA was added, followed by vortexing. Then, 10 ul 100 mM $Na_2HPO_4$ was added, followed by vortexing. 10 ul 100 mM $CaCl_2$ was added, followed by vortexing. Finally, 380 ul 100% ethanol was added, followed by vortexing. While the suspension was stirred vigorously, 3 ul were pipetted onto plastic fliers (projectiles). Particles were allowed to dry onto fliers for at least 15 minutes before bombarding.

VII. Bombarding Cell Cultures

The petri plate containing the cell filters was inverted onto the platform on top of the stage, and centered over the particle flight opening. The clear lid was placed over the top of the platform. A microprojectile was placed onto the breech pin and the breech closed. The "arm" button was pushed to fill the reservoir with the appropriate amount of helium gas (usually 1800–1900 psi). The vacuum on the chamber was pulled to ~27 mm. After the vacuum was turned off, and the "arm" and "fire" buttons were pushed. The "arm" button was then pushed to the "off" position. Each filter was usually shot twice.

VIII. Post-bombardment Culture and Selection

After bombardment the cells were kept in the dark overnight. The next day, filters were removed from plasmolysis medium and placed on 1 MS medium. Selection was applied 7–10 days post-bombardment for suspension cells and after 14 days for callus cells. Cells were scraped off the filters and spread onto the surface of plates containing 1 MS plus 2 mg/liter methotrexate. (Transformants were obtained by initially selecting at 4 mg/liter methotrexate also.) Plates were incubated in the dark for several weeks. Resistant colonies that arise after a few weeks were transferred to 1 MS+4 mg/l methotrexate. Colonies that continue to proliferate for about 3–4 weeks are then transferred to "0.5 MS" maintenance medium: MS salts, vitamins, iron, 3% sucrose, 0.7% agar, 0.5 mg/liter 2,4-D. Tissue was subcultured onto this medium biweekly until embryogenic structures appeared or tissue seemed suitable for regeneration.

IX. Regeneration

Tissue was transferred to MS medium containing either 3 mg/liter BAP or 1 mg/liter NAA +5 mg/liter CA, and plates were moved to the light. After 2–4 weeks, tissue was transferred to MS medium without hormones. Shoots that appeared were placed in containers with either MS medium without hormones or MS medium with 0.5 mg/liter NAA. When sufficient root and shoot growth had occurred, plantlets were transferred to soil and placed in a phytotron.

X. Transformant Analysis

About 20 mg callus tissue was used for PCR analysis. DNA was extracted using a quick phenol/chloroform:isoamyl alcohol method and 2 ul was used per reaction. Primers were designed to amplify the region from the 5' end of the adh gene to the 3' end of the dhfr gene.

XI: Transformation of wheat by microprojectile bombardment of Type II callus derived from Type M callus.

Type II callus derived from Type M callus was obtained from immature embryos of the spring wheat genotype UC703 using the methods described above. The resulting callus line, called UC703-0612, was friable, embryogenic, and serially propagated in vitro. A microprojectile device was used to deliver DNA to the Type II callus. Two plasmids were co-precipitated onto micrometer sized gold particles and introduced into plant cells. One plasmid, pSOG30, is a β-glucuronidase (gus) expression vector derived from plasmid pBI121, purchased from Clontech Laboratories, Palo Alto, Calif. Intron 6 of the maize Adh 1 gene was amplified by PCR from plasmid pB428, described in "Bennetzen et al, Proc. Natl. Acad. Sci., U.S.A. 81:4125–4128 (1987)" and ligated into the BamH1 site of pBI121, which is between the CaMV35S promoter and the Gus gene. A 17 bp maize chlorotic mottle virus (MCMV) leader, described in "Lommel et al., Virology 181:382–385 (1991)", was inserted into the 35S-Gus gene non-translated leader. The final gene fusion contains the structure: 35S promoter-Adh 1 intron 6-MCMV leader-Gus-Nos terminator, all in the pUC19 vector backbone. The second plasmid, pSOG35, is a dihydrofolate reductase (dhfr) expression vector. This construct was derived by fusing the 35S promoter, Adh 1 intron 6, and MCMV leader described above to the dhfr gene from plasmid pHCO, described in "Bourouis and Jarry, EMBO J. 2:1099–1104 (1983)". The final gene fusion contains the structure: 35S promoter-Adh 1 intron 6-MCMV leader-dhfr-Nos terminator, all in the pUC 19 vector backbone.

Two weeks after bombardment, cells were transferred to callus maintenance medium containing 4 mg/liter methotrexate. Resistant colonies that proliferated were subcultured over a period of months and then regenerated in the absence of methotrexate. PCR analysis was done on callus samples to confirm the presence of the dhfr gene. One colony, SJ3-2A, produced a $T_0$ plant (SJ3-2A-1) in vitro that was eventually transferred to soil and grown in the greenhouse. Leaf samples from this plant were assayed for gus enzyme activity using standard protocols (Jefferson, Plant Molecular Biology Reporter Vol. 5, No. 4, 1987) and were positive. DNA was extracted from this plant and Southern analysis confirmed the presence of the dhfr gene.

Plant SJ3-2A-1 was grown to maturity in a greenhouse and was pollinated with wild-type pollen from UC703 plants. Two seeds developed, from which two immature embryos were excised and germinated. One rescued embryo produced one $T_1$ plant (known as RE1), while the second rescued embryo was placed on callus induction medium and subsequently produced ten $T_1$ plants, two of which are known as RE2 and RE3. Leaf samples from RE 1 were assayed for gus enzyme activity and were positive. PCR analysis for presence of 35S promoter sequences was done on RE1, RE2, and RE3 and all three plants were positive. Southern analysis was done to probe for the presence of the gus and gene in these three progeny plants, and all three were positive for the gene. $T_1$ plants RE1, RE2, and RE3 (also known as RE2B) were pollinated with wild type UC703 pollen to produce $T_2$ plants. Many seeds developed on each plant and immature embryos were rescued and germinated in vitro. Fluorimetric gus assays were done and transformants were identified from a segregating population.

XII: Transformation of wheat by microprojectile bombardment of immature embryos and isolation of transformants without the use of a selectable marker or selection agent.

Immature embryos of genotype UC703, 0.75–1.5 mm in length, were excised and plated onto MS medium containing 5 mg/liter 2,4-D and 3% sucrose, 30 embryos per plate.

Two plasmids were co-precipitated onto micrometer size gold particles and introduced into plant cells by the DuPont Biolistics® device using standard techniques as published in the operations manual. One plasmid, pCIB3089, contains the cauliflower mosaic virus 35S promoter fused to the cDNA of the maize anthocyanin regulatory gene B-peru, with intron #2 from alcohol dehydrogenase 1 gene placed between the 3' end of the coding sequence and 5' to the 35S terminator sequence. The other plasmid, pCIB4436, contains the CaMV 35S promoter fused to the cDNA of the maize anthocyanin regulatory gene C1, with intron #9 of the maize PEP-carboxylase gene placed between the 3' end of the coding sequence and 5' to the 35S terminator. Together, these two genes perform as a scorable marker for transformation.

After 22 days, embryos were scored for Type I callus response and callus was transferred to a proliferation medium. Twenty of ninety-four embryos showed a Type I callus response. Tissue from eleven of the twenty responding embryos was transferred to plant regeneration medium about one month later. Eleven plants were grown to maturity in the greenhouse and all plants set seed. One plant (JN11-1800-3#1) produced reddish-colored seed, presumably caused by expression of one or more of the inserted regulaory genes. Five DNA samples were obtained from this plant and PCR analysis was done to check for the presence of the 35S promoter, the C1 gene, and the B-peru gene. The PCR results were positive for these sequences in three independent reactions.

In order to analyze the $T_1$ generation, fifty-seven immature embryos from this PCR positive plant were excised, germinated, and analyzed. Of these, forty-one $T_1$ plants were PCR positive for both the B-peru and C1 genes. Twenty-two seed-derived $T_1$ plants were also found to be PCR positive for these genes. Southern analysis was done on the parent plant and three PCR positive $T_1$ progeny. All were positive for B-peru and negative for C1 by this analysis. The T2 generation was grown in the greenhouse for seed production.

XIII: Transformation of wheat by microprojectile bombardment of immature embryos using a high sucrose plasmolysis step prior to gene delivery.

Immature embryos (0.75–1.0 mm length) of the wheat genotype UC703 were plated on Murashige and Skoog medium (Physiologia Plantarum 15: 473–497, 1962) containing 3 mg/liter 2,4-D and 3% sucrose. Twenty embryos were placed on each plate of medium. Three days later the immature embryos were transferred to the same medium but containing an additional 15% sucrose in order to plasmolyze the tissue prior to gene delivery.

Plasmids pAct1/gus and pSOG35 was precipitated onto micrometer size gold particles using standard procedures. Each plate of embryos were shot twice with the DuPont Biolistics® helium device using a burst pressure of 900 psi. A total of four target plates were bombarded using the standard 80 mesh screen and four plates were shot without the screen in place. Approximately 4 hours after bombardment the embryos were transferred back to Murashige and Skoog medium containing 3% sucrose. Approximately one month later the embryo explants with developing embryogenic callus were transferred to regeneration medium (Murashige and Skoog +1 mg/liter NAA, 5 mg/liter GA), further containing 2 mg/liter methotrexate as a selection agent. After approximately one month, developed shoots were transferred to larger sterile containers known as "GA7s" which contained half-strength Murashige and Skoog salts, 2% sucrose, and 2 mg/liter methotrexate.

DNA was extracted from four plants isolated and grown as described. PCR analysis for the presence of the 35S promoter showed that two plants were positive. These transgenic plants were labelled SJ30-44 and SJ30-121. Plant SJ30-121 was assayed for gus activity and shown to be strongly positive. The plants were transferred to soil for propagation in the greenhouse. Fertile transformed plants were obtained.

XIV: Transformation of wheat by microprojectile bombardment of immature embryos using a high maltose plasmolysis step prior to gene delivery.

Immature embryos (0.75–1.0 mm length) of gentotype UC703 were plated on Murashige and Skoog medium containing 3 mg/l 2,4-D and 3% sucrose. After approximately 4 hours the embryos were plated with the embryo axis side down onto plates containing Murashige and Skoog medium with 15% maltose, 3% sucrose and 3 mg/l 2,4-D overlayed with a filter paper supported slab of agarose containing the same components. The embryos were allowed to plasmolyze for 2–3 hours before bombardment.

DNA of pAct1/gus and pSOG35 was precipitated onto micrometer size gold particles using standard procedures. Four target plates with 20 embryos per target were shot twice with the DuPont Biolistics® helium device using a burst pressure of 1100 psi. The plates were shot with an 80 mesh screen in place between the carrier stage and the target. The targets were placed in the dark at 26C for 24 hours after bombardment before the slabs with the embryos were laid onto plates containing Murashige and Skoog medium with 3 mg/l 2,4-D and 3% sucrose. The individual embryos were removed from the slabs and placed directly on fresh medium of the same composition after another 48 hours.

Approximately 6 weeks after gene delivery, the responding tissue was placed on Murashige and Skoog medium with 3 mg/l 2,4-D and 3% sucrose with 0.2 mg/l methotrexate for a 3 week period. The tissue was then placed on a regeneration medium comprised of Murashige and Skoog medium with 1 mg/l zeatin riboside and 1 mg/l methotrexate. After 2 weeks, regenerating plantlets were placed in sterile containers called "GA7s" with half-strength Murashige and Skoog salts, 2% sucrose, 1 mg/l NAA and either 4 or 8 mg/l methotrexate.

DNA was extracted from leaf tissue of four plants derived from 2 different target plates and PCR was run for the the presence of the dhfr gene. All 4 were positive for the presence of the dhfr. Two of the plants were sent to the greenhouse for propagation.

XV: Development of improved embryogenic cultures of wheat using previously regenerated material as a culture source.

To use regenerated plants as the starting material for such improved cultures plants were regenerated from the maltose-induced friable callus described above on a Murashige and Skoog medium with 3 mg/l BAP and 3% sucrose. This maltose-induced friable callus was a Type II cell culture labelled UC703-0612, thawed out from cryopreservation and placed on a maintenance medium (Murashige and Skoog medium +1 mg/l 2,4-D +3% sucrose) prior to regeneration. For embryo culture, wheat spikes were collected from the regenerated plants, sterilized with 10% Clorox solution for 10 min, and rinsed several times with sterile water. Immature embryos, 1–2 mm in size, were removed from caryopses under a dissecting microscope and cultured on a Murashige and Skoog medium with either 5 or 10 mg/l 2,4-D and 13.7 g/l maltose, or on a Murashige and Skoog medium with 2 mg/l 2,4-D and 3% sucrose. This newly induced friable callus, now recycled, was transferred to a Murashige and Skoog medium with 1 mg/l 2,4-D and 3% sucrose for maintenance or bombardment experiments. The above plant regeneration and callus induction process were then repeated to produce future generations of friable callus.

As a control, embryos from wild-type plants were collected and cultured on the same maltose medium. The induction frequency of a friable and embryogenic callus from the embryos was recorded and are shown below.

|  | TC Medium | No. Embryos Cultured | No. Embryos Producing Friable Callus | % Embryos Producing Friable Callus |
| --- | --- | --- | --- | --- |
| Recycled lines | 10MS13.7M | 50 | 14 | 28 |
|  | 5MS13.7M | 50 | 11 | 22 |
| Control | 10MS13.7M | 50 | 2 | 4 |
|  | 5MS13.7M | 50 | 3 | 6 |

To use seed derived from regenerated plants as the starting material, a Type II cell culture (UC703-0612), which was produced from an embryo grown on a maltose-containing medium, was thawed out from cryopreservation and placed on a maintenance medium (Murashige and Skoog medium +1 mg/l 2,4-D +3% sucrose). The callus was then placed on a medium containing Murashige and Skoog basal salts and 3 mg/l 6-BAP for plant regeneration. Seeds were harvested from the regenerated plants and then germinated in soil. For embryo culture, wheat spikes were collected from the seed-derived plants, sterilized with 10% Clorox solution for 10 min, and rinsed several times with sterile water. Immature embryos, 1–2 mm in size, were removed from caryopses under a dissecting microscope and cultured on a Murashige and Skoog medium with 2 or 10 mg/l 2,4-D and 13.7 g/l maltose, or on a MS medium with 2 mg/l 2,4-D and 3% sucrose. The induced friable callus was transferred to a MS medium with 1 mg/l 2,4-D and 3% sucrose for maintenance or bombardment experiments.

As a control, embryos from wild-type plants were collected and cultured on the same maltose medium. The induction frequency of a friable and embryogenic callus from the embryos was recorded and are shown below.

| TC Date | # Embryos Cultured | # Embryos Produced Friable Callus | % Embryos Produced Friable Callus |
| --- | --- | --- | --- |
| 6/18 | 97 | 12 | 12 |
| 6/21 | 260 | 52 | 20 |
| 7/12 | 140 | 34 | 24 |

-continued

| TC Date | # Embryos Cultured | # Embryos Produced Friable Callus | % Embryos Produced Friable Callus |
|---|---|---|---|
| 7/14 | 120 | 24 | 20 |
| 7/19 | 280 | 56 | 20 |
| Total | 897 | 178 | 20 |
| Control | 280 | 0 | 0 |

XVI: Transformation of wheat using a recycled embryogenic culture.

A recycled, embryogenic callus line labelled 0612RC was developed as described in the above example. Callus was prepared for bombing by stirring and plasmolyzing for 2–3 hours in liquid Murashige and Skoog medium containing 1 mg/l 2,4-D, 3% sucrose and 0.6M sorbitol in a ratio of 1 part cells to 16 parts medium. Each target was prepared by using a vacuum filter appartus to affix 3 ml of the cell mixture to glass fiber filters which were then placed onto solid Murashige and Skoog medium with 1 mg/l 2,4-D, 3% sucrose and 0.4M sorbitol.

DNA from plasmid pTG48 (ant43/gus/35Sdhfr) was precipitated onto micrometer size gold particles using 0.1M $CaCl_2$ and 0.1M $NaH_2PO_4$. Each target was shot twice with the microprojectile device described in U.S. application Ser. No. 07/772,435 using a gas pressure of 1900 psi. After gene delivery, the filters and cells were removed from the sorbitol medium and placed on Murashige and Skoog medium with 1 mg/l 2,4-D and 3% sucrose approximately 24 hours later and allowed to grow for 17 days before placing on the same medium but with 1 mg/l methotrexate included. The selection level was increased to 2 mg/l methotrexate 17 days later.

Approximately 7 weeks later colonies were removed from the original selection plates to fresh medium containing 1 mg/l methotrexate. The colonies were identified as being positive for the presence of the dhfr gene by PCR. The tissue was bulked up and maintained on a reduced 2,4-D level (0.5 mg/l) to encourage somatic embryo maturation. Plantlets were regenerated by using Murashige and Skoog medium with 5 mg/l GA and 1 mg/l NAA. Some tissue was regenerated by placing on Osmorafts in liquid Murashige and Skoog media with 3% sucrose and 10 mg/l zeatin. Plantlets were transferred to sterile containers called "GA7s" containing ½-strength Murashige and Skoog salts, 2% sucrose and 0.5 mg/l NAA approximately 20 weeks after bombardment. Plants were transferred to the greenhouse for propagation. Five plants were analyzed by Southerns and the presence of the dhfr gene was confirmed.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for producing stably transformed fertile wheat plants, said method comprising:

isolating an immature embryo from a wheat plant;

plating said immature embryo on growth medium;

delivering a DNA sequence of interest by high velocity microprojectile bombardment to said immature embryo up to 10 days after excision;

treating said immature embryo in a manner sufficient to produce embryogenic callus;

selecting for transformed cells; and, regenerating fertile transformed plants.

2. The method of claim 1 wherein said DNA sequence of interest comprises a dihydrofolate reductase coding sequence from a bacterial gene.

3. The method of claim 1, wherein said DNA delivery comprises subjecting the immature embryo to multiple shots of DNA coated particles.

4. The method of claim 1, wherein said selecting step comprises growing said transformed cells on medium comprising methotrexate or hygromycin.

5. The method of claim 4, wherein said medium comprises methotrexate.

\* \* \* \* \*